(12) United States Patent
Dormanen et al.

(10) Patent No.: US 8,882,744 B2
(45) Date of Patent: Nov. 11, 2014

(54) QUICK-CONNECT OUTFLOW TUBE FOR VENTRICULAR ASSIST DEVICE

(75) Inventors: Christopher P. Dormanen, Howell, MI (US); Sunil K. Dasara, Ann Arbor, MI (US); Takeshi Tsubouchi, Tokyo (JP)

(73) Assignee: Thoratec Corporation, Pleasanton, CA (US)

( * ) Notice: Subject to any disclaimer, the term of this patent is extended or adjusted under 35 U.S.C. 154(b) by 133 days.

(21) Appl. No.: 13/405,784

(22) Filed: Feb. 27, 2012

(65) Prior Publication Data

US 2013/0225909 A1 Aug. 29, 2013

(51) Int. Cl.
*A61M 25/16* (2006.01)
*A61M 39/10* (2006.01)

(52) U.S. Cl.
CPC ........... *A61M 39/1011* (2013.01); *A61M 39/10* (2013.01)
USPC ............................................. 604/533; 600/16

(58) Field of Classification Search
CPC ............ A61M 39/10; A61M 39/1011; A61M 2039/1077
USPC ............................................ 604/533; 600/16
See application file for complete search history.

(56) References Cited

U.S. PATENT DOCUMENTS

| | | |
|---|---|---|
| 5,810,708 A | 9/1998 | Woodard et al. |
| 6,001,056 A | 12/1999 | Jassawalla et al. |
| 6,050,987 A | 4/2000 | Rosenbaum |
| 6,264,248 B1 | 7/2001 | Marbach |
| 6,319,231 B1 | 11/2001 | Andrulitis |
| 7,048,681 B2 | 5/2006 | Tsubouchi et al. |
| 7,172,550 B2 | 2/2007 | Tsubouchi |
| 7,303,553 B2 * | 12/2007 | Ott ................................ 604/533 |
| 7,824,358 B2 | 11/2010 | Cotter et al. |
| 2004/0171905 A1 | 9/2004 | Yu et al. |
| 2007/0134993 A1 | 6/2007 | Tamez et al. |
| 2012/0095281 A1 | 4/2012 | Reichenbach et al. |
| 2012/0209057 A1 | 8/2012 | Siess et al. |
| 2013/0096364 A1 | 4/2013 | Reichenbach et al. |

OTHER PUBLICATIONS

International Preliminary Report on Patentability of PCT/US13/25703, mailed Jan. 10, 2014, 10 pages.

* cited by examiner

*Primary Examiner* — Christopher D Koharski
*Assistant Examiner* — Philip Edwards
(74) *Attorney, Agent, or Firm* — Kilpatrick Townsend & Stockton LLP

(57) ABSTRACT

An outflow conduit for a cardiac assist pump has a connector at one end comprised of a main sleeve configured to mate with a pump outlet port. A plurality of prongs extend from the sleeve. Each prong has a distal end with a claw and is bendable so that its respective claw expands over a lip and enters the groove of the outlet port. A lock nut is movable between a retracted position and a locking position. In the retracted position, a soft interconnect is obtained. In the locking position, the claws are prevented from escaping over the lip and a hard interconnect is obtained.

15 Claims, 12 Drawing Sheets

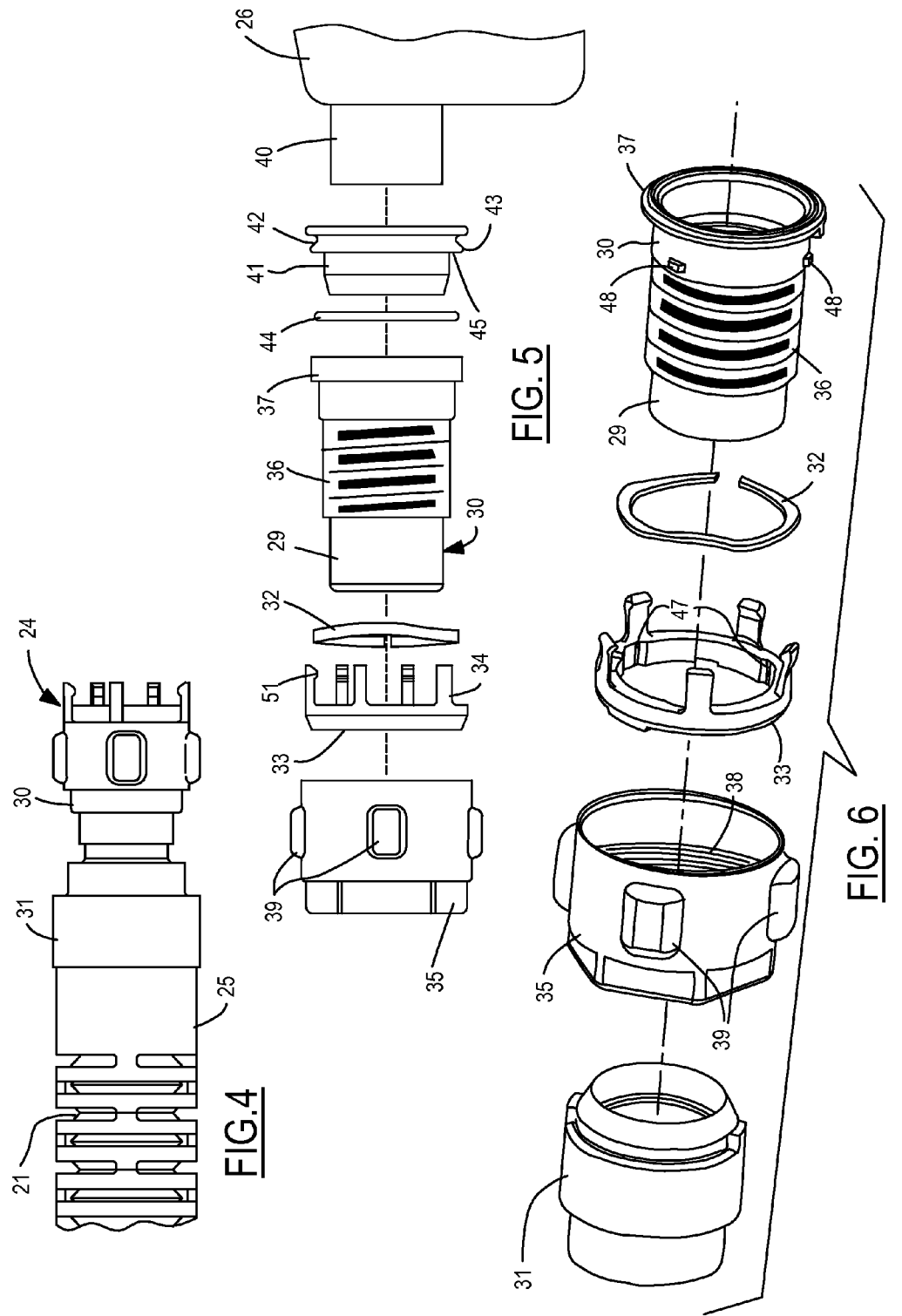

QUICK-CONNECT OUTFLOW TUBE FOR VENTRICULAR ASSIST DEVICE

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to cardiac assist systems, and, more specifically, to a connector for attaching an outflow conduit to an implanted pump.

A heart pump system known as a left ventricular assist system (LVAS) can provide long term patient support with an implantable pump associated with an externally-worn pump control unit and batteries. The LVAS improves circulation throughout the body by assisting the left side of the heart in pumping blood. One such system is the DuraHeart® LVAS system made by Terumo Heart, Inc., of Ann Arbor, Mich. A typical LVAS system employs a centrifugal pump, an inflow conduit coupling the pump to the left ventricle, and an outflow conduit coupling the pump to the aorta. During implantation, one end of the outflow conduit is mechanically fitted to the pump via a connector and the other end is surgically attached to the patient's ascending aorta by anastomosis. Examples of the inflow and outflow conduits are shown in U.S. Pat. No. 7,172,550, issued Feb. 6, 2007, entitled "Adjustable Coupling Mechanism for the Conduit on a Ventricular Assist Device," which is incorporated herein by reference.

Because the LVAS is implanted in the body of a patient, it is desirable to minimize the size of each of its components. In order to improve patient outcomes by reducing the time and complexity of the implantation procedure, it is also desirable to provide a simple mechanism for making fast and reliable connections to the pump.

SUMMARY OF THE INVENTION

The present invention provides a quick-connect mechanism for attaching an outflow conduit to the outlet of a cardiac assist pump. An interconnection of the outflow conduit to the pump outlet is achieved using simple movements not requiring excessive application of force. The placement of the connector includes a "soft" connection which fixes the outflow conduit to the pump but allows limited movement (e.g., rotation) of the connector while staying fixed to the outlet. Once a final configuration of the implanted components is achieved, the connector is moved to a "hard" connection, again without necessitating application of excessive force.

In one aspect of the invention, an implantable cardiac assist apparatus comprises an implantable pump having a cylindrical outlet port with a groove defining a lip. An outflow conduit conveys blood from the pump. A connector is fixed to one end of the outflow conduit. The connector is comprised of a main sleeve joined to the outflow conduit and configured to mate with the outlet port. The main sleeve has a longitudinal axis. A plurality of prongs extend substantially parallel to the longitudinal axis, wherein each prong has a distal end with a claw. Each prong is bendable so that its respective claw deflects over the lip to be captured in the groove when the main sleeve is advanced onto the outlet port. A lock nut is movable between a retracted position and a locking position. The connector is movably retained on the outlet port by the plurality of prongs when the claws are positioned in the groove and the lock nut is in the retracted position. The connector is rigidly retained on the outlet port when the lock nut is advanced to the locking position.

BRIEF DESCRIPTION OF THE DRAWINGS

FIG. 4 is a plan view showing a proximal end of the outflow conduit with the connector.

FIG. 5 is an exploded, side view showing the component parts of the connector.

FIG. 6 is an exploded, perspective view showing the component parts of the connector.

DETAILED DESCRIPTION OF PREFERRED EMBODIMENTS

Figure 1:
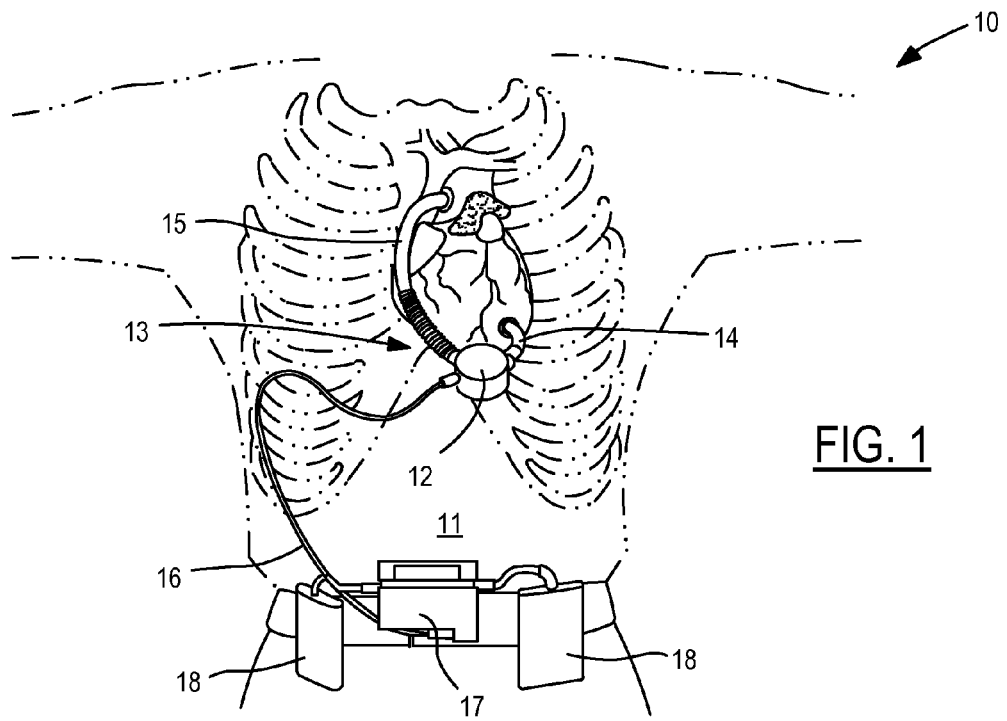
FIG. 1 is a front view of a left ventricular assist system having a pump implanted into a patient.

Referring to FIG. 1, a patient 10 is shown in fragmentary front elevational view. Surgically implanted into the patient's abdominal cavity or pericardium 11 is the pumping portion 12 of a ventricular assist device 13. An inflow conduit 14 conveys blood from the patient's left ventricle into the pumping portion 12, and an outflow conduit 15 conveys blood from the pumping portion 12 to the patient's ascending thoracic aorta. A power cable 16 extends from the pumping portion 12 outwardly of the patient's body via an incision to a compact controller 17. A power source, such as battery packs 18, is worn on a belt about the patient's waist and connected with controller 17.

Figure 2:
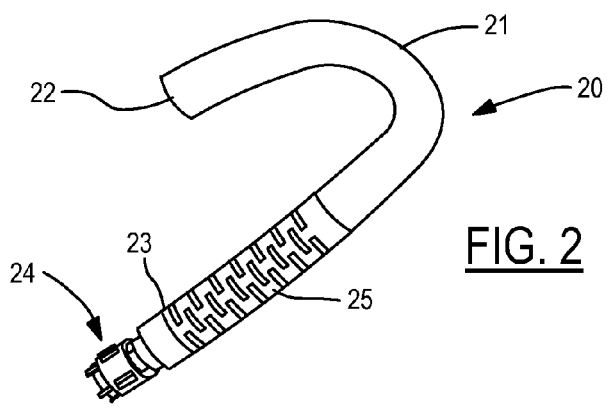
FIG. 2 is a perspective view of an embodiment of an outflow conduit and connector of the present invention.

FIG. 2 shows an outflow conduit assembly 20 which includes a woven Dacron graft 21. A first end 22 of graft 21 may be sutured to the patient's aorta, for example. A second end 23 of graft 21 is joined with a connector 24. A plastic cage 25 is preferably mounted over graft 21 at second end 23 to prevent graft 21 from collapsing or kinking in an area where graft 21 must make its sharpest bend after implantation in a patient (e.g., to curve around the heart itself).

Figure 3:
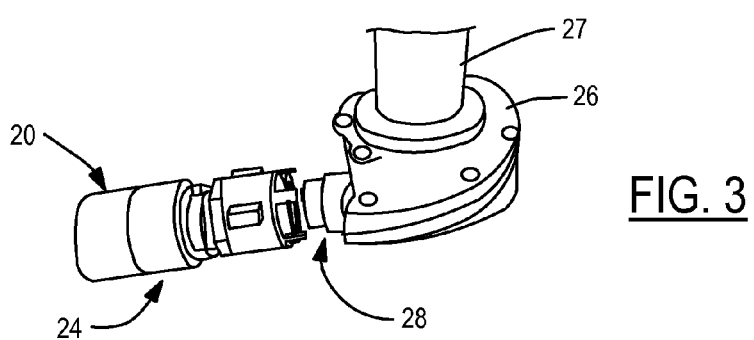
FIG. 3 is perspective view showing an outflow connector and pump.

FIG. 3 shows a pump 26 with an inlet conduit 27 which is inserted into the left ventricle. Pump 26 has an outlet port 28 which receives connector 24. In one type of surgical procedure, inlet conduit 27 and pump 26 may be joined with the ventricle prior to final placement and attachment of outflow conduit 20. Prior to and during attachment of inlet conduit 27 to the heart, it may sometimes be desirable to have pre-installed outflow conduit 20 onto outlet port 28. If pre-installed, it may also be desirable for connector 24 to be 1) easily repositionable on outlet port 28 for proper orientation, and 2) easily removable in order to obtain back-bleeding through outflow conduit 20 in order to expel air. The present invention provides a "soft" connection during implantation to make it removable and repositionable and a "hard" connection to ensure a secure and immovable retention following implantation.

As shown in FIGS. 4 and 5, connector 25 includes a main sleeve 30 formed as a generally cylindrical, metal body. A crimp fitting 31 interconnects main sleeve 30 with graft 21 and cage 25. Main sleeve 30 also carries a spring washer 32, a base ring 33 having a plurality of prongs 34, and a lock nut 35. Sleeve 30 has a threaded region 36 and an outward flange 37 at the end proximate to the pump outlet port.

As shown in FIG. 5, the pump outlet port includes a tube 40 extending from the external housing of pump 26. An adaptor 41 having a circumferential groove 42 defining a lip 43 is fitted over tube 40. Adaptor 41 may be welded to tube 40 and pump 26, for example. A seal 44 is received by adaptor 41 against a sealing surface 45. Seal 44 is compressed between the outlet port and flange 37 when a connection is made as described below.

The exploded view in FIG. 6 shows crimping connection 31 which connects with end 29 of sleeve 30. Sleeve 30 has projections 48 spaced from flange 37. Spring washer 32 and base ring 33 are installed between flange 37 and projections 48. Locking nut 35 has internal threads 38 which are threaded onto external threads 36 of sleeve 30. Grippers 39 extend on the outer surface of lock nut 35 to facilitate grasping by the fingers during manual rotation of lock nut 35.

Figure 7:
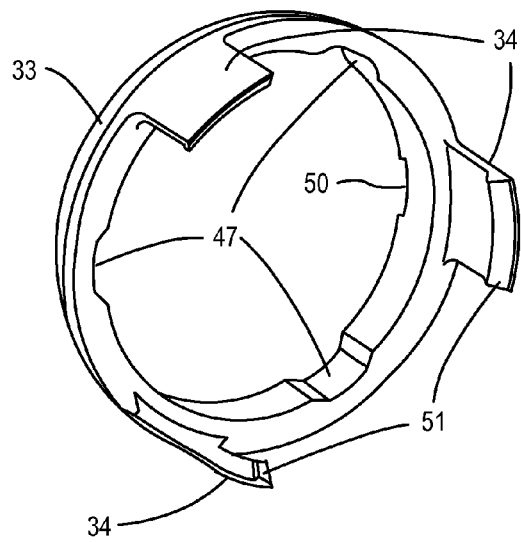
FIG. 7 is a perspective view of the base ring and claws.
Figure 8:
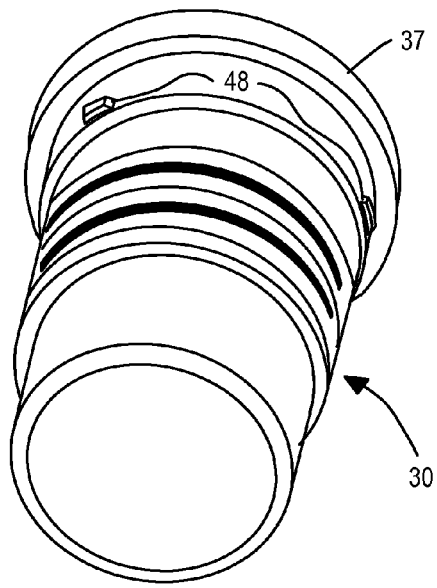
FIG. 8 is a perspective view of the main sleeve.
Figure 9:
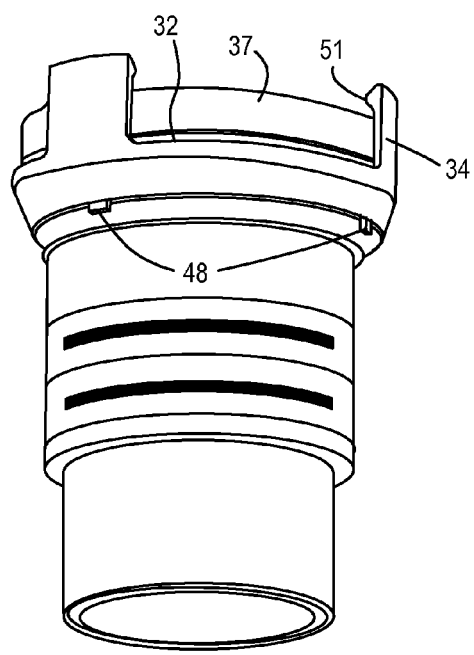
FIG. 9 is a perspective view showing the base ring mounted to the main sleeve.
Figure 10:
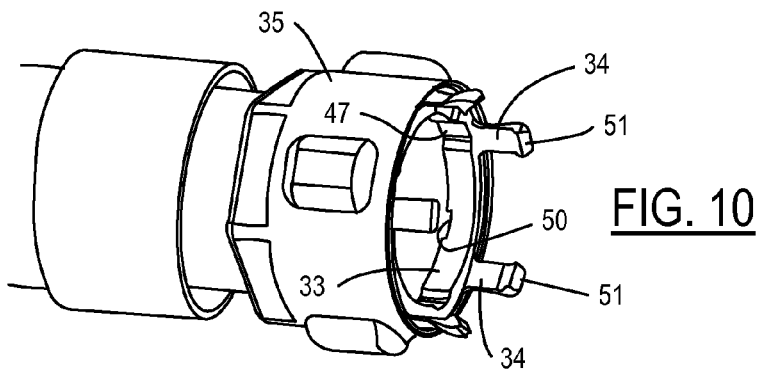
FIG. 10 is a perspective view of the connector.

As best shown in FIG. 7, base ring 33 includes recesses 47 on its inside diameter. FIG. 7 shows an embodiment with a different number of prongs 34 than in FIGS. 4-6. The spacing between recesses 47 matches the spacing of projections 48 on sleeve 30 as shown in FIG. 8. Spring washer 32 is preferably formed as a wavy C-ring so that its inside diameter allows it to fit over projections 48. After placing spring washer 32 proximate to an inside edge of flange 37, base ring 33 is slipped onto sleeve 30 toward flange 37 by aligning grooves 47 with projections 48 and compressing it against spring washer 32. Then base ring 33 is rotated so that projections 48 align with matching notches 50 located between partial recesses 47. Spring washer 32 tries to expand so that it locks base ring 33 in position. Thus, prongs 34 extend from base ring 33 over flange 37 as shown in FIG. 9. Because of the foregoing arrangement, base ring 33 is keyed with projections 48 on main sleeve 30 so that base ring 33 and prongs 34 are held firmly in place on the end of sleeve 30. Prongs 34 have respective claws 51 at their distal ends. Each prong extends substantially parallel to a longitudinal axis of sleeve 30, and each prong 34 is outwardly bendable so that respective claws 51 are expandable to interconnect with the pump outlet port as explained below. FIG. 10 illustrates the relative position of base ring 33 to locknut 35 with the main sleeve being removed for clarity.

Figure 11:
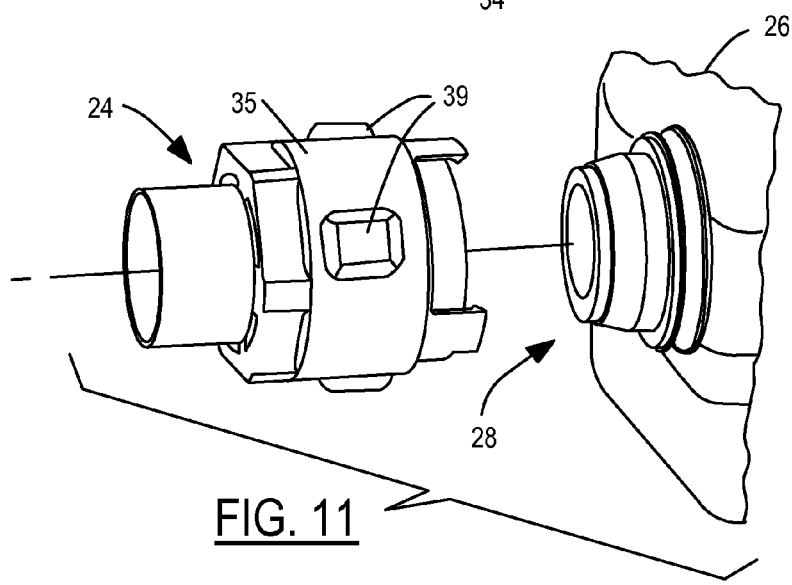
FIG. 11 is a perspective view showing the connector approaching the pump outlet port.
Figure 12:
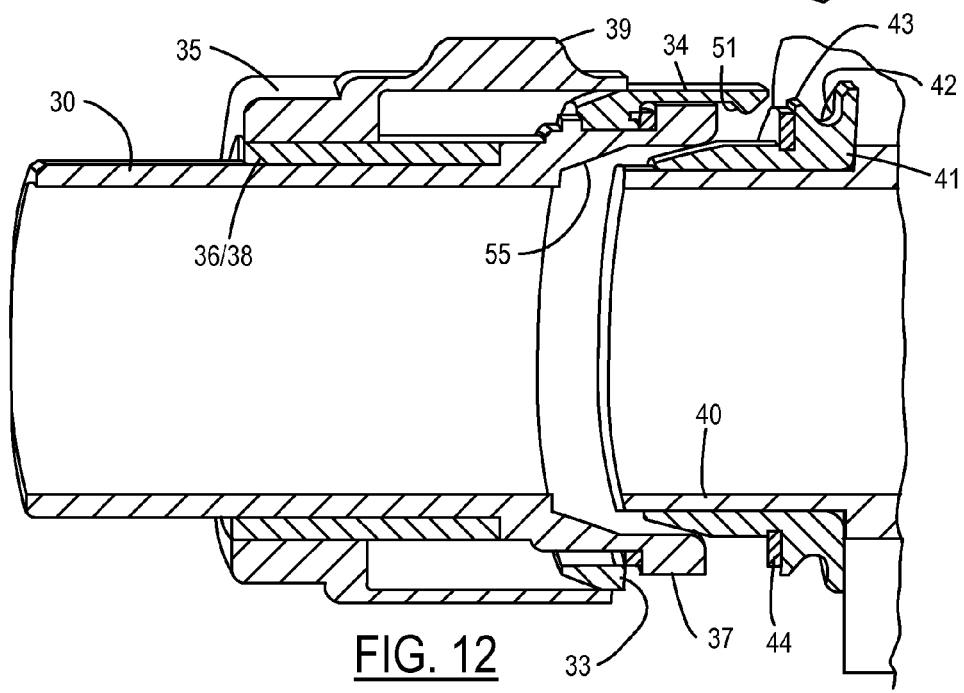
FIG. 12 is a cross-sectional view of the connector sliding onto the pump outlet port.
Figure 13:
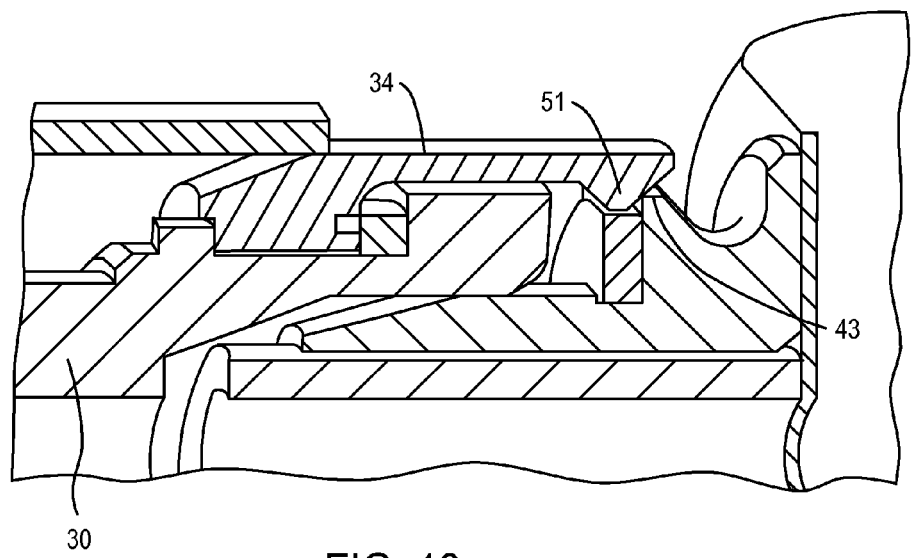
FIG. 13 is a cross section of the connector and outlet port just before a "soft" connection is made.
Figure 14:
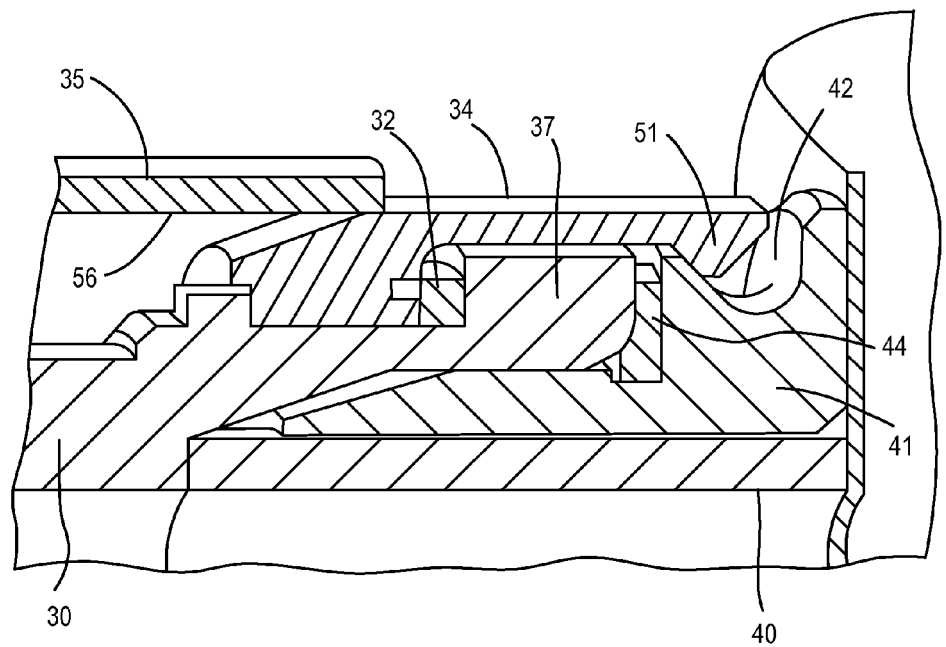
FIG. 14 is a cross section of the connector and outlet port after a "soft" connection has been made.

FIG. 11 shows connector 24 being aligned with outlet port 28 on pump 26 in order to initiate an interconnection. FIG. 12 is a cross-sectional view showing the further progression of a connection, wherein main sleeve 30 is advanced coaxially toward tube 40 and adaptor 41. Locknut 35 is movable via the cooperation of threaded areas 36/38 between a retracted position as shown in FIG. 12 and a locking position to be described in connection with FIG. 15. With locknut 35 in the retracted position, prongs 34 are unrestrained so that they are bendable outwardly. Main sleeve 30 has an inner receiving surface 55 complementary with the surface of adaptor 41. Claws 51 are positioned to interact with adaptor 41 such that they bend outwardly in order to slide over lip 43 and enter groove 42. FIG. 13 illustrates claw 51 at the beginning of its interact with lip 43. A sloped edge of claw 51 guides claw 51 outward as main sleeve 30 slides to the right in FIG. 13. As sleeve 30 becomes fully seated against adaptor 41 and seal 44, claw 51 enters groove 42 as shown in FIG. 14. Sleeve 30 and tube 40 provide a continuous inside diameter for a smooth flow of blood. Seal 34 is compressed between adaptor 41 and sleeve 30 to prevent leakage. In the "soft connect" condition shown in FIG. 14, the connector is movably retained on the outlet port. In other words, the connector is retained to the outlet port while being repositionable, e.g., by rotation of claws 51 circumferentially along circumferential groove 42 to allow adjustment of the positioning of the outflow conduit prior to making a hard, immovable connection. During implantation, a surgeon adjusts the position of the outflow conduit until a final orientation is reached. During a procedure, the surgeon may also remove the connector after the other end of the outflow conduit is attached to the aorta for the purpose of back-bleeding to remove air from the outflow conduit. The removal and reconnection/realignment of the connector can be done easily with minimal force.

Figure 15:
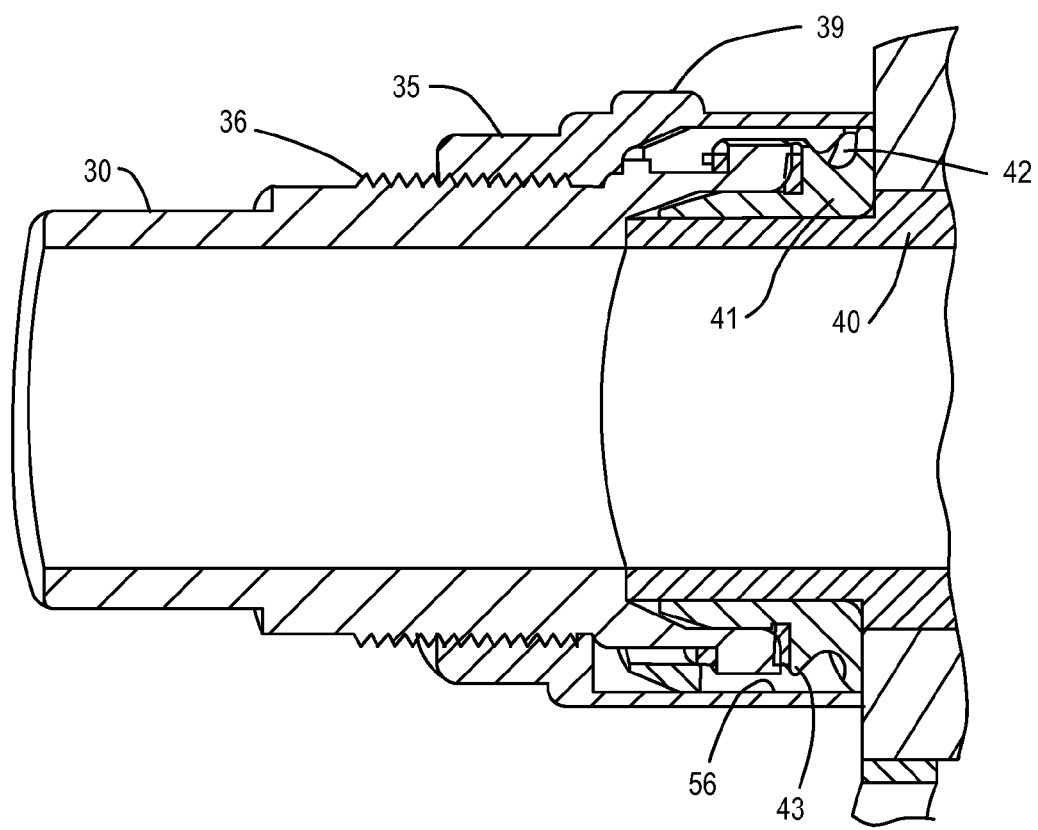
FIG. 15 is a cross section of the connector and outlet port after a "hard" connection has been made.

FIG. 15 shows the "hard connect" state of the connector wherein locknut 35 is advanced to the locking position, whereby a bearing surface 56 on the inside diameter of lock nut 35 bears against prongs 34 to prevent their outward bending. Since claws 51 cannot expand over lip 43 and are instead clamped down against groove 42, the connector is rigidly retained on the outlet port. Rotating locking nut 35 to traverse the threads and move it back to the retracted position would allow further adjustment of the position on the outlet port. The complementary tapering of claw 50 and circumferential groove 42 allow easy removal by pulling the connector away from the outlet port (e.g., by grasping lock nut 35) so that prongs 34 expand at their ends and claws 51 expand over lip 43. In the hard locked position, the taper of claws 51 and groove 42 pull sleeve 30 toward the pump so that flange 37 compresses seal 44.

Figure 16:
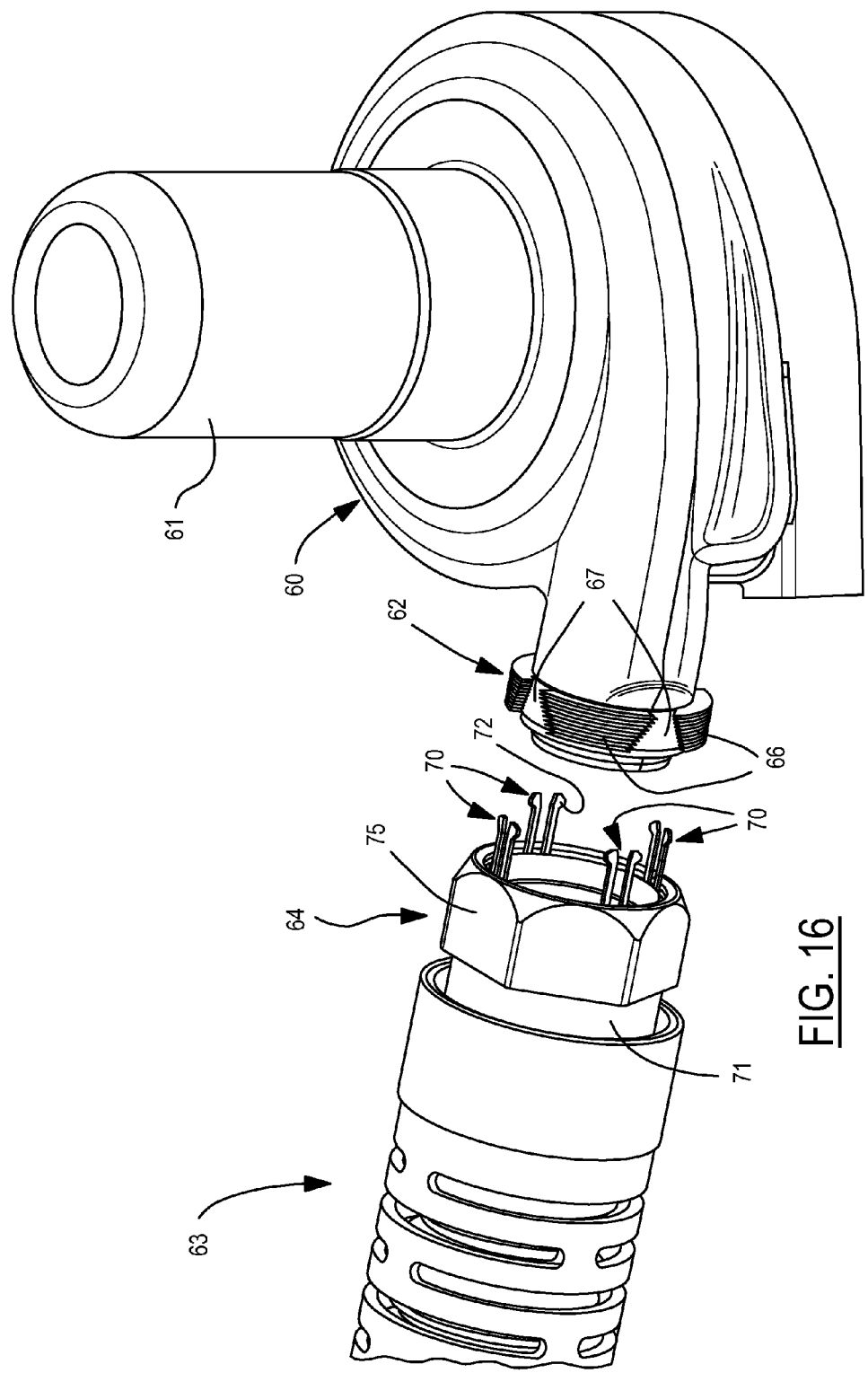
FIG. 16 is a perspective view of another embodiment of the connector and outlet port prior to interconnecting them.

FIGS. 16-21 show an alternative embodiment wherein axially-extending prongs are received in axially-extending grooves instead of a circumferential groove. FIG. 16 shows a pump 60 including an inflow conduit 61 and an outlet port 62 for receiving an outflow conduit 63. A connector 64 is capable of "soft" and "hard" connections with outlet port 62.

Figure 17:
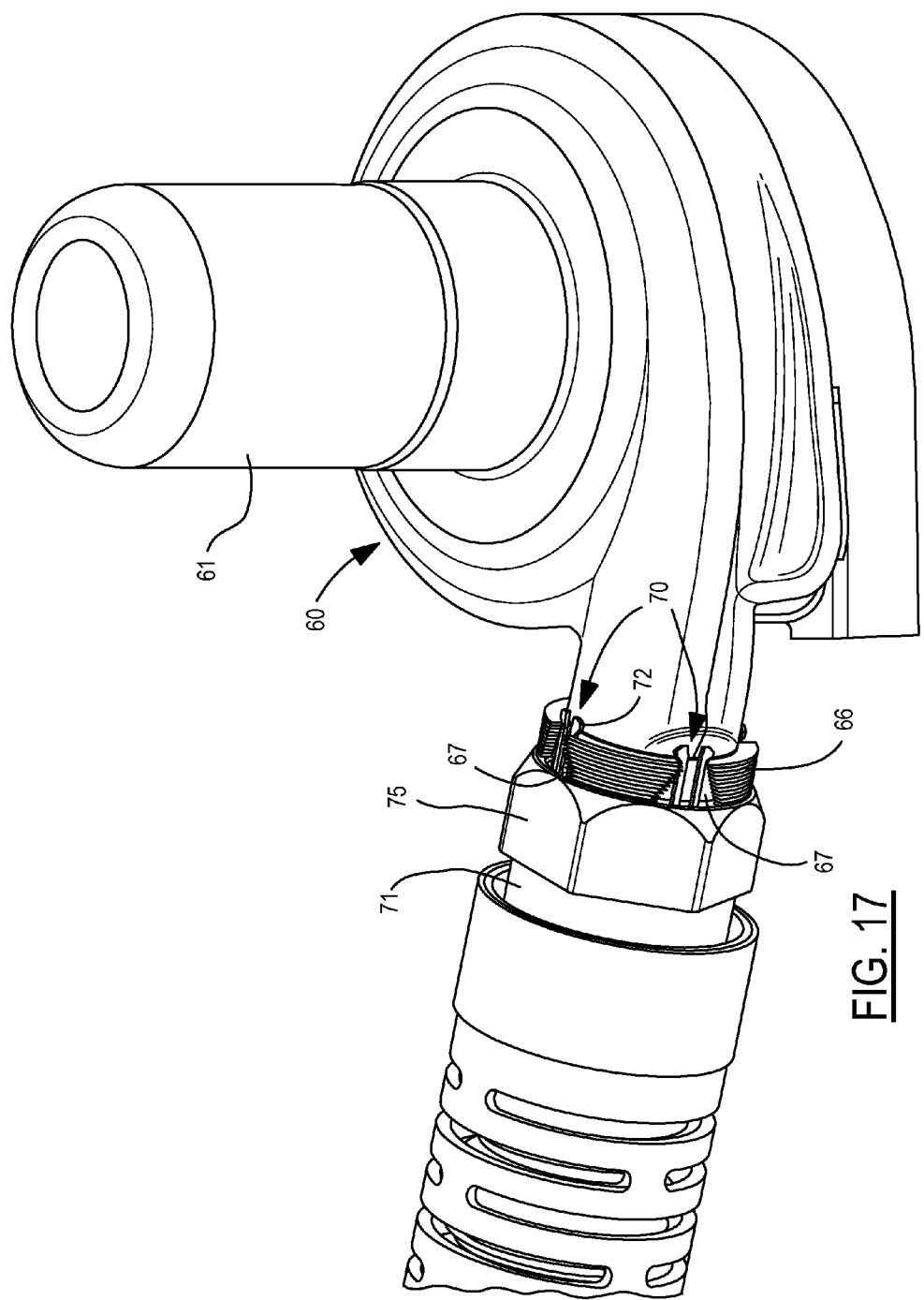
FIG. 17 is a perspective view of the connector and outlet port of FIG. 16 in a "soft" connection.

Outlet port 62 has external threads 66 that are configured to mesh with a lock nut 75. Portions of thread 66 are removed in order to create a series of axial grooves 67 spaced around the periphery of outlet port 62. Connector 64 has a plurality of prongs 70 extending axially from a main sleeve 71. Preferably, prongs 70 extend in matching pairs, each with oppositely-directed claws 72. Each pair of prongs 70 aligns with a respective groove 76. FIG. 17 shows the soft connection wherein each pair of prongs 70 is captured within a corresponding groove 67. Lock nut 75 is shown in a retracted position which allows main sleeve 71 and outflow conduit 63 to rotate while being implanted during surgery.

Figure 18:
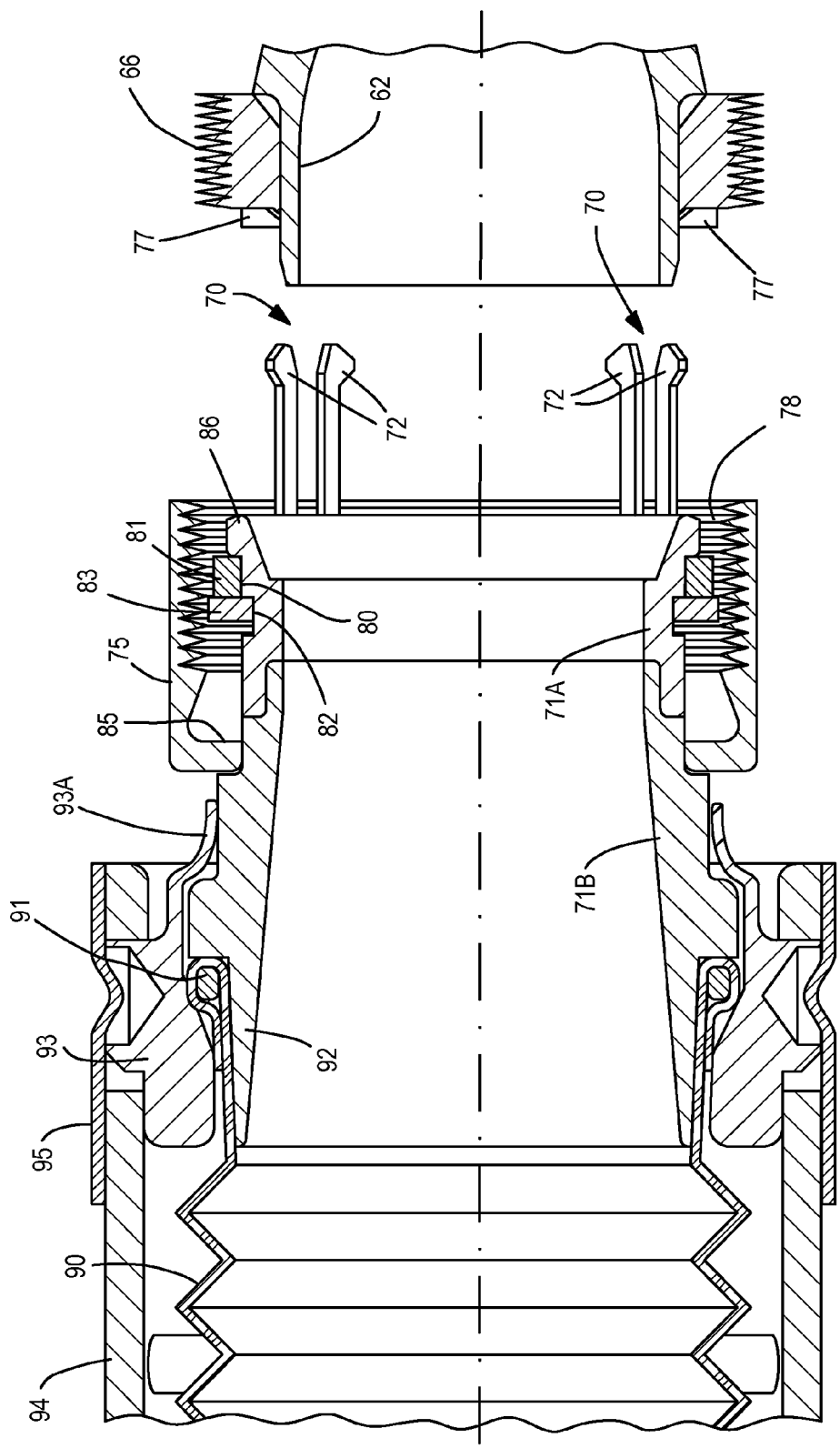
FIG. 18 is a cross-sectional view of the connector and outlet port of FIG. 16.

The cross section of FIG. 18 shows the elements of the connector and outlet port in greater detail. A ring carrying threads 66 may be welded to outlet port 62. A compression seal 77 is installed at the distal end of threads 66. Main sleeve 71 includes a proximal section 71A and a distal section 71B, each cylindrical in shape and which may be welded together. The outer edge of proximal section 71A has a stepped configuration with a first pocket 80 which receives a base ring 81 (from which prongs 70 extend, similar to the previous embodiment). The fit between base ring 81 and pocket 80 is sufficiently loose that ring 81 is able to rotate circumferentially in pocket 80. A deeper pocket 82 adjacent to pocket 80 receives a C-shaped or expandable clip 83 for keeping base ring 81 in place. To assemble the connector, base ring 81 with prongs 70 is slid onto proximal sleeve section 71A until it stops in pocket 80. Clip 83 is inserted into pocket 82, and then lock nut 75 is slid onto proximal sleeve section 71A (e.g., until an inside shoulder 85 contacts clip 83. Then proximal sleeve section 71A is welded to distal sleeve section 71B. A conventional graft portion of the outflow conduit is attached by crimping. In particular, a graft 90 with a cylindrical collar 91 is fitted over a distal end 92 of main sleeve 71 and attached by a crimp ring 93 by pinching its end 93A over a corresponding ridge on sleeve section 71B. A protective cage 94 is held in place over an outer edge of crimp ring 93 by a cover sleeve 95 which is crimped onto ring 93.

Figure 19:
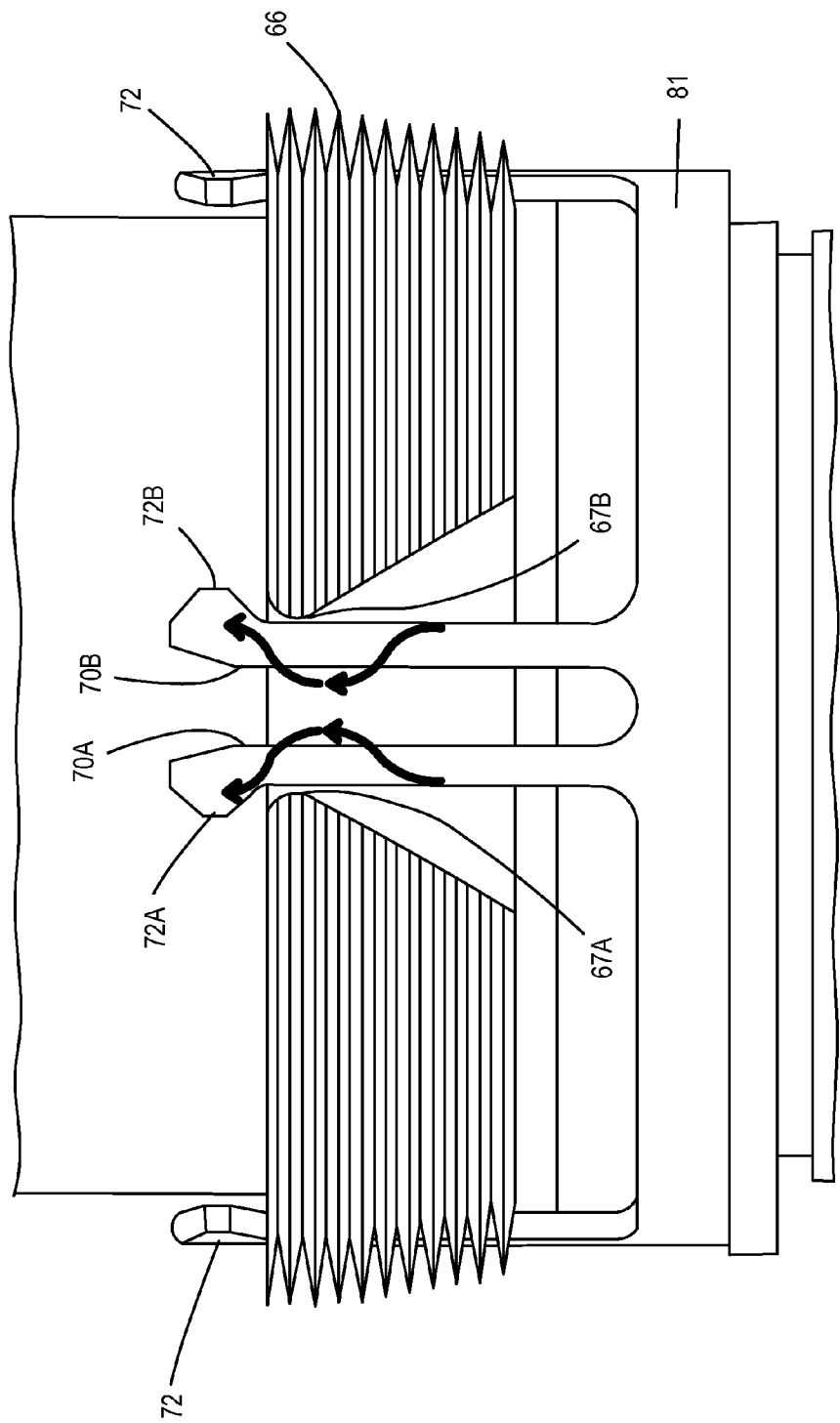
FIG. 19 is a side, plan view showing the prongs being inserted into a groove on the outlet port.

FIG. 19 illustrates the manner in which a soft connection is obtained by advancing prongs 70 into grooves 67 on outlet port 62. A groove 67 has opposing ramp-shaped sides to form lips 67A and 67B. Claws 72A and 72B at the ends of prongs 70A and 70B are gradually pinched together as they advance through groove 67, and they expand apart after passing beyond lips 67A and 67B, respectively. Prongs 70 and base ring 81 are retained in the position shown in FIG. 19 in a loose condition since some amount of play is permitted as long as the lock nut is not tightened (the lock nut is not shown in FIG. 19 for clarity). Main sleeve is allowed to rotate within base ring 81, thereby facilitating adjustment by a surgeon during implantation. It is also possible to disconnect prongs 70 from outlet port 62, but the required force is higher since the axial distance over which prongs 70A and 70B must squeeze together is much shorter.

Figure 20:
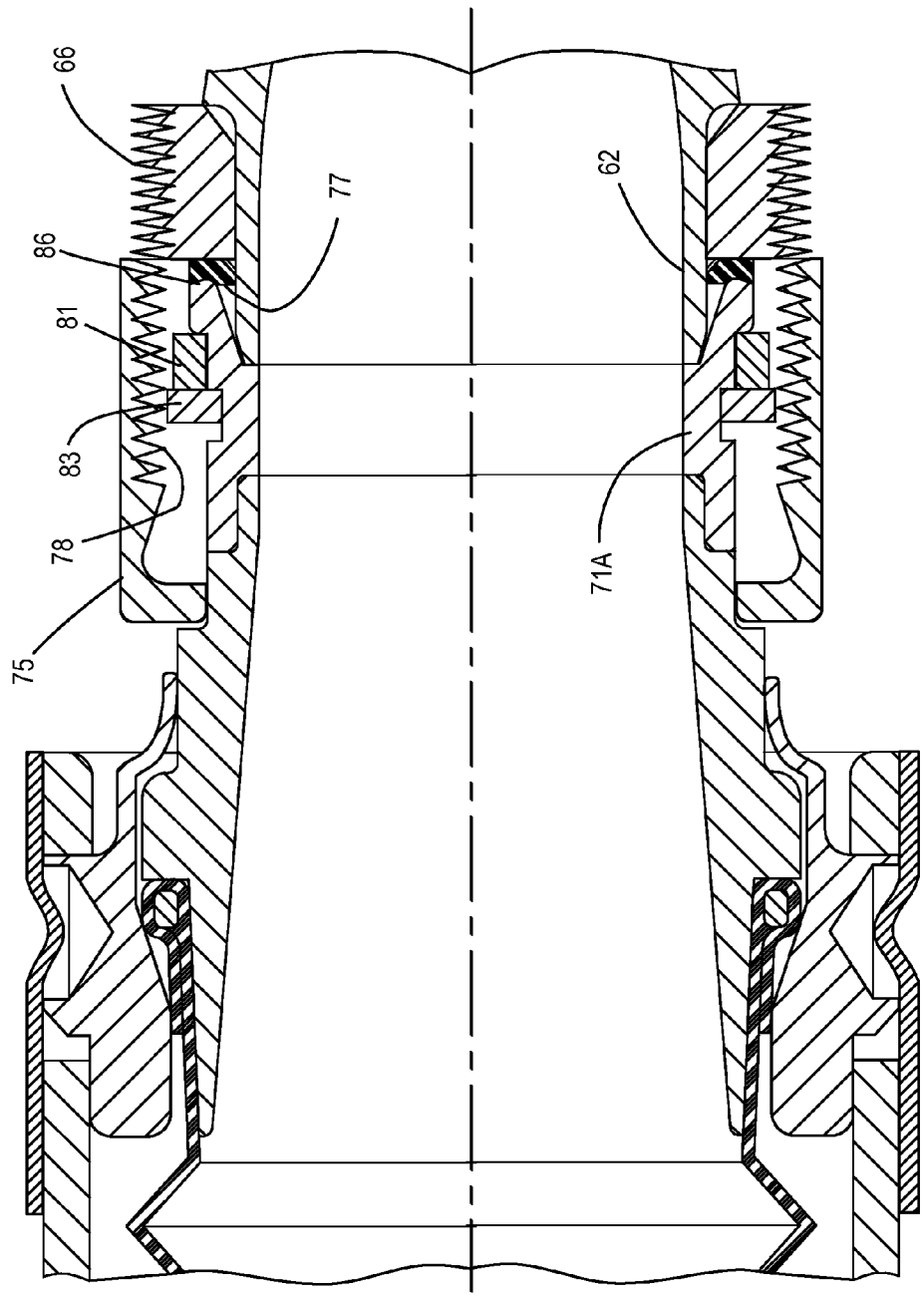
FIG. 20 is a cross-section of the connector and outlet port of FIG. 16 in a "soft" connection.
Figure 21:
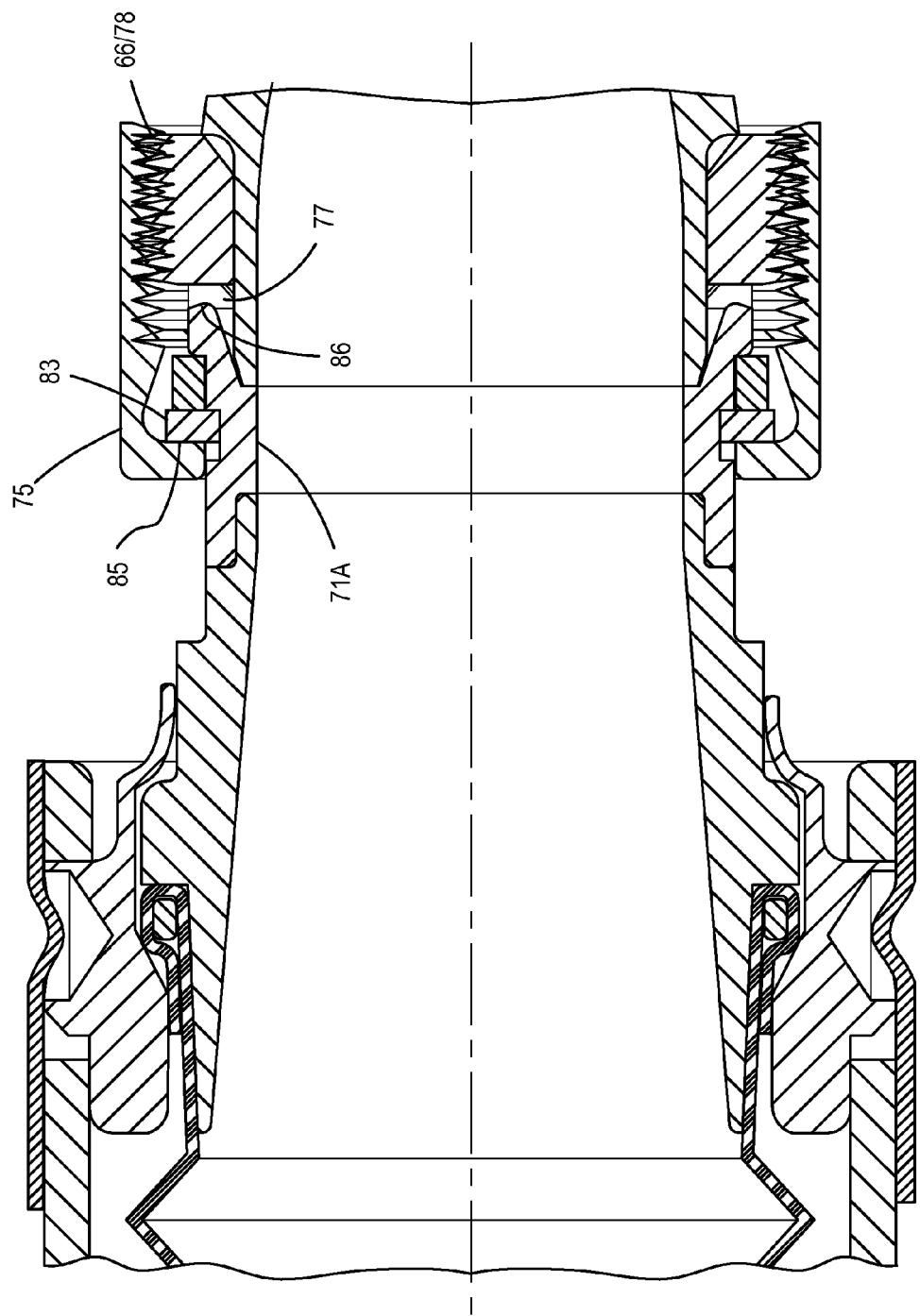
FIG. 21 is a cross-section of the connector and outlet port of FIG. 16 in a "hard" connection.

FIG. 20 shows lock nut 75 in its retracted position and proximal sleeve section 71A inserted on outlet port 62. Proximal edge 86 of sleeve section 71A gently contacts seal 77 so that rotation is permitted. In FIG. 21, lock nut 75 has been turned onto threads 66 so that it has advanced to its locking position. Shoulder 85 of lock nut 75 is drawn against clip 83 by the action of threads 66/78. Proximal edge 86 compresses seal 77 to prevent leakage of blood around the connector.

What is claimed is:

1. An implantable cardiac assist apparatus comprising:
    an implantable pump having a cylindrical outlet port with a groove defining a lip;
    an outflow conduit for conveying blood from the pump; and
    a connector fixed to one end of the outflow conduit, wherein the connector is comprised of:
        a main sleeve joined to the outflow conduit and configured to mate with the outlet port, the main sleeve having a longitudinal axis;
        a plurality of prongs extending substantially parallel to the longitudinal axis, wherein each prong has a distal end with a claw, and wherein each prong is bendable so that its respective claw deflects over the lip to be captured in the groove when the main sleeve is advanced onto the outlet port; and
        a lock nut movable between a retracted position and a locking position;
    wherein the connector is movably retained on the outlet port by the plurality of prongs when the claws are positioned in the groove and the lock nut is in the retracted position, and is rigidly retained on the outlet port to form a seal between surfaces of the outlet port and surfaces of the main sleeve when the lock nut is advanced to the locking position, wherein the plurality of prongs are further comprised of a base ring that is retained on the main sleeve, wherein the outlet port comprises a plurality of threads on an outer circumference for receiving the lock nut, wherein the groove is comprised of a plurality of circumferentially-spaced axial grooves recessed into the plurality of threads, wherein each axial groove includes at least one respective lip defined by a circumferential narrowing of the respective axial groove, wherein each axial groove receives at least one respective prong, wherein the main sleeve is rotatable within the base ring when the lock nut is in the retracted position, and wherein the base ring is clamped into a fixed position when the lock nut is in the locking position.

2. The apparatus of claim 1 wherein the groove and the lip extend circumferentially around the outlet port.

3. The apparatus of claim 2 wherein the lock nut has a bearing surface with an inner diameter, wherein when the lock nut is in the retracted position then the bearing surface is axially offset from the prongs, and wherein when the lock nut is in the locking position then the bearing surface bears against the prongs and prevents the claws from expanding over the lip.

4. The apparatus of claim 3 wherein the main sleeve includes an outward flange proximate to the outlet port, and wherein the prongs each extend from the base ring over the outward flange.

5. The apparatus of claim 4 wherein the base ring and the main sleeve are keyed so that the base ring is compressed against the outward flange.

6. The apparatus of claim 5 further comprising a spring washer between the base ring and the outward flange.

7. The apparatus of claim 6 wherein the spring washer is comprised of a wavy C-ring.

8. The apparatus of claim 2 further comprising a seal mounted on the outlet port for compressing between the outlet port and the outward flange.

9. The apparatus of claim 8 wherein at least one of the claws or the circumferential groove are tapered so that when the claws are fully seated into the circumferential groove by the lock nut being moved to the locking position then the main sleeve is compressed against the seal.

10. The apparatus of claim 1 further comprising a seal mounted on the outlet port for compressing between the outlet port and the main sleeve.

11. The apparatus of claim 1 wherein the lock nut is threaded onto the main sleeve.

12. A method of connecting an outlet port of an implantable cardiac assist pump to an outflow conduit, comprising:
    advancing a main sleeve of a connector onto the outlet port, wherein the connector includes a plurality of prongs that each have a claw and the main sleeve is advanced so that at least one claw expands over a lip of the outlet port and enters a groove of the outlet port, and wherein a lock nut of the connector is in a retracted position during the advancing step;

adjusting the position of the outflow conduit to a particular orientation, wherein the connector is movably retained on the outlet port during the adjusting step as a result of the claw being positioned in the groove; and moving the lock nut from the retracted position to a locking position to prevent the at least one claw from expanding over the lip, and so that the connector is rigidly retained on the outlet port to form a seal between surfaces of the outlet port and surfaces of the main sleeve;

wherein the plurality of prongs are further comprised of a base ring that is retained on the main sleeve, wherein the outlet port comprises a plurality of threads on an outer circumference for receiving the lock nut, wherein the groove is comprised of a plurality of circumferentially-spaced axial grooves recessed into the plurality of threads, wherein each axial groove includes at least one respective lip defined by a circumferential narrowing of the respective axial groove, wherein each axial groove receives at least one respective prong, wherein the adjusting step is comprised of rotating the main sleeve within the base ring when the lock nut is in the retracted position.

13. The method of claim 12 wherein the groove and the lip extend circumferentially around the outlet port, and wherein the adjusting step is comprised of rotating the connector with respect to the outlet port by sliding the claws circumferentially along the circumferential groove.

14. The method of claim 13 wherein a seal member is positioned between the main sleeve and the outlet port, and wherein at least one of the claws or the circumferential groove are tapered so that when the claws are fully seated into the circumferential groove by the lock nut being moved to the locking position then the main sleeve is compressed against the seal member.

15. A method of connecting an outlet port of an implantable cardiac assist pump to an outflow conduit, comprising:

advancing a main sleeve of a connector that is coupled to the outflow conduit onto the outlet port, wherein a lock nut of the connector is in a retracted position during the advancing step;

adjusting the position of the outflow conduit to a particular orientation, wherein the connector is movably retained on the outlet port during the adjusting step; and moving the lock nut from the retracted position to a locking position so that the connector is rigidly retained on the outlet port to form a seal between surfaces of the outlet port and surfaces of the main sleeve;

wherein the connector includes a plurality of prongs that each have a claw and the main sleeve is advanced so that at least one claw expands over a lip of the outlet port and enters a groove of the outlet port, wherein the plurality of prongs are further comprised of a base ring that is retained on the main sleeve, wherein the outlet port comprises a plurality of threads on an outer circumference for receiving the lock nut, wherein the groove is comprised of a plurality of circumferentially-spaced axial grooves recessed into the plurality of threads, wherein each axial groove includes at least one respective lip defined by a circumferential narrowing of the respective axial groove, wherein each axial groove receives at least one respective prong, wherein the main sleeve is rotatable within the base ring when the lock nut is in the retracted position, and wherein the base ring is clamped into a fixed position when the lock nut is in the locking position.

* * * * *